United States Patent [19]
Eardley et al.

[11] 3,948,906
[45] Apr. 6, 1976

[54] CEPHALOSPORIN COMPOUNDS

[75] Inventors: Stephen Eardley, Southport, England; James Kennedy, Montrose, Scotland; Alan Gibson Long, Greenford, England

[73] Assignee: Glaxo Laboratories Limited, Greenford, England

[22] Filed: July 12, 1974

[21] Appl. No.: 487,984

Related U.S. Application Data

[60] Continuation of Ser. No. 383,838, July 30, 1973, abandoned, which is a continuation of Ser. No. 186,802, Oct. 5, 1971, abandoned, which is a division of Ser. No. 752,180, Aug. 8, 1968, Pat. No. 3,658,799.

[30] Foreign Application Priority Data

Aug. 21, 1967 United Kingdom............... 38494/67

[52] U.S. Cl............................. 260/243 C; 424/246

[51] Int. Cl.[2]....................................... C07D 501/18
[58] Field of Search................................ 260/243 C

[56] References Cited
UNITED STATES PATENTS 3,766,177  10/1973  Webber et al. ................. 260/243 C Primary Examiner—Nicholas S. Rizzo
Attorney, Agent, or Firm—Bacon & Thomas

[57] ABSTRACT

7β-Amino- and acylamidoceph-3-em-4-carboxylic acids having at the 3-position a halo-, formyloxy-, isothiocyanato- or haloacetoxymethyl group and salts and esters thereof. These compounds are useful as starting compounds for preparing 7α-acylamidoceph-3-em-4-carboxylic acids having a group at the 3-position, other than 3-acetoxymethyl, by reaction with a nucleophile. The compounds prepared have modified antibiotic activity.

1 Claim, No Drawings

CEPHALOSPORIN COMPOUNDS

This is a continuation of application Ser. No. 383,838, filed July 30, 1973, now abandoned, which is in turn a continuation of application Ser. No. 186,802, filed Oct. 5, 1971, now abandoned, which latter application is in turn a division of application Ser. No. 752,180, filed Aug. 13, 1968, and now U.S. Pat. No. 3,658,799.

This invention is concerned with improvements in or relating to the production of analogues of sporin C.

The compounds in this specification are generally named with refernce to cepham which has the structure

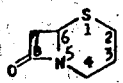

(see J.A.C.S. 1962, 84, 3400).

7β-Acylamidoceph-3-em-4-carboxylic acids having a group at the 3-position, other than 3-acetoxymethyl, are generally of interest in that they possess modified antibiotic activity, as compared with the corresponding 3-acetoxymethyl-7β-acyl-amidoceph-3-em-4-carboxylic acid, for example N-[7β-(2'-thienylacetamido)-ceph-3-em-3-ylmethyl]pyridinium-4-carboxylate having the accepted name cephaloridine possesss advantageous antibiotic activity as compared with 3acetoxymethyl-7β-(2'-thienylacetamido)ceph-3-em-4-carboxylic acid British Patent No. 1,012,943 describes and claims the direct displacement of the acyloxy group of the 3-acyloxy-methyl substituent of such ceph-3-em-4-carboxylic acids by certain compounds of a nucleophilic nature. This type of process, however, is unsuccessful with some nucleophiles and in other cases low yields are obtained. Reaction with sulphur-containing nucleophiles often proceeds in good yields, but factors such as the low solubility of some of the products and deficiencies in activity against gram-negative organisms, render the products less useful as antibiotics. British Patent No. 912,541 describes and claims the direct replacement of the acetoxy group of cephalosporin C compounds by compounds such as pyridine to form cephalosporin $C_A$ compounds. This method leads to low yields of the desired $C_A$ compounds.

We have now discovered that a wider range of nucleophiles may be used for substitution reactions at the exocyclic methylene group if the 3-acyloxymethyl group is first hydrolysed to the 3-hydroxymethyl group which is then reesterified (if necessary after protective esterification of the 4-carboxy group) with certain acids hereinafter defined, and then allowed to react with the nucleophile. The process provides a useful alternative to the method of said Bristish Patents Nos. 1,012,943 and 912,541, furthermore, the method enables one to prepare cephalosporin analogues difficultly accessible by direct displacement of the acetoxy group.

According to the present invention therefore we provide a process for the preparation of a cephalesporin analogue which includes the step of reacting a ceph-3-em-4-carboxylic acid, or a derivative thereof, having the group RHN— at the 7β-position, wherein R represents a hydrogen atom or a carboxylic acyl group, said ceph-3-em-4-carboxylic acid or derivative having the group

at the 3-position (so that the ceph-3-em-4-carboxylic acid or derivative used as starting material has the formula

where Q is the remainder of the cephalosporin molecule) such that the acid HX has a pKa of not more than 4.0, preferably not more than 3.5, and X does not contain a sulphur atom linked to the hydrogen atom, with a compound having a nucleophilic atom, e.g., a carbon, nitrogen, oxygen or sulphur atom, under conditions effective to displace the group X by the nucleophile.

Where R is a hydrogen atom it may first be protected, e.g. by acylation, with a group which is subsequently removed. Alternatively, the hydrogen atom may be left unprotected in which event it may be involved in subsequent reactions. In general we prefer to use compounds in which R is an acyl group.

The pKa values refer to aqueous solution at 25°C.

The specific classes of compounds having nucleophilic atoms will be referred to or convenience as "carbon, nitrogen, oxygen or sulphur nucleophiles" in the following.

The group X is preferably one of three main types, depending whether a halogen atom, oxygen atom or nitrogen atom is directly attached to the Q-CH$_2$-group (where Q is as hereinbefore defined); these three types of group will be discussed in turn under the respective headings: halogens; oxygen leaving-groups; and nitrogen leaving-groups.

HALOGENS (X = Cl, Br, or I)

When X represents a halogen atom, we have found that the 4-carboxy group may or may not be esterified. Since esters are generally without substantial antibiotic activity, and moreover since the corresponding isomeric ceph-2-em-4-carboxylic acids are also generally without substantial antibiotic activity, it is desirable to use as esterifying group a group which can be readily introduced and removed without appreciable Δ³→ 2 isomerisation (which is known to be likely to occur in such reactions). Preferred esterifying groups include the diphenylmethyl, the β,β,β-trichloroethyl and t-butyl groups; the diphenylmethyl group can be readily introduced by means of diphenyldiazomethane, and removed e.g. by means of a mixture of trifluoroacetic acid and anisole at room temperature whilst the β,β,β-trichloroethyl group may be removed by means of zinc and acetic acid.

The 3-CH$_2$X compounds, where X represents Cl or Br, can be prepared from the corresponding 3-CH$_2$OH compounds by standard methods for the replacement of —OH by Cl or Br. For example, the 3-CH$_2$Cl compounds can be prepared from the corresponding 3-CH$_2$OH compounds by reaction with thionyl chloride, acid chlorides such as N,N-dialkyl-or N,N-diaryl-chlorosulphinamides, e.g. N,N-dimethyl-chlorosulphinamides, or alkyl chlorosulphites. The 3-CH$_2$Br compounds can be similarly prepared by reaction of the corresponding bromo-compounds with the 3-CH$_2$OH compounds or by reaction of the latter with PBr$_3$ and pyridine. The 3-CH$_2$I compounds may be prepared from the corresponding chlorides and bromides e.g. by reaction with an alkali metal iodide.

The 3-CH$_2$OH compounds can be prepared for example by hydrolysis of the corresponding 3-CH$_2$.O.-COCH$_3$ compounds. The hydrolysis is preferably effected enzymatically, using, for example, wheat germ esterase or an esterase of the genus Rhizobium, as described in Belgian Patent Specification No. 671,692, or an esterase derived from orange peel, as described in British Specification No. 966,222.

3-Halomethyl-7β-acylaminoceph-3-em-4-carboxylic acids, the halogen atom being chlorine, bromine, or iodine and salts thereof e.g. with alkali metals such as sodium or potassium and with organic bases, and esters thereof, where the esterifying group is preferably one which is readily introducible and removable without appreciable $\Delta^3 \rightarrow \Delta^2$ isomerisation, are novel compounds and constitute a feature of the invention.

OXYGEN LEAVING-GROUPS

Another class of starting materials useful in the process according to the invention has the partial formula

Q—CH$_2$—O—

(where Q is as hereinbefore defined). This class includes esters of acetic acid derivatives having at least one electron-withdrawing substituent on the α-carbon atom, and esters of nuclear substituted benzoic acids, the nuclear substituent also being of the electron-withdrawing type. Thus the acid HX may be any of the various haloacetic acids (dichloroacetic acid being particularly preferred), methoxy-, alkylthio-, or cyano-acetic acid, glyoxylic acid, phenylpropiolic acid, a hemi-ester of malonic or oxalic acid, phenylglyoxylic acid, or a substituted phenylglyoxylic acid, the substituent(s) being for example one or more halogen atoms (F, Cl, Br, or I), methoxy groups or methyl groups. When the acid HX is a substituted benzoic acid, the choice of the substituent in the benzene ring will be influenced to some extent by a consideration of the stereochemistry of the benzoic acid HX. In general we prefer the phenyl group to be substituted in the 3- or 4-position rather than the 2-position since substitution of the 2-position gives rise to the maximum steric hinderance. Thus possible substituents include, for example, 4-methyl, 3- chloro or bromo, 3-, or 4- nitro or 3,5-dinitro, 3-, or 4-trifluoromethyl, 4-carbamoyl, 3-, or 4-(esterified carboxyl), or 3-, or 4-cyano.

The acid HX may also be formic acid.

When the group X contains a reactive centre, e.g., an active chlorine atom as in a dichloroacetoxy group, the incoming nucleophile may attack at this centre also. Under such circumstances, it is desirable to use a corresponding excess of the incoming nucleophile, e.g., two equivalents excess when dichloroacetoxy is displaced.

The starting materials having the partial formula

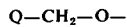
Q—CH$_2$—O—

(where Q is as hereinbefore defined) are conveniently prepared by acylation of a cephalosporanic acid derivative having a 3-hydroxymethyl group. The acylating agent is preferably a reactive derivative of an acid such as a keten (where this exists), an acid halide, e.g. a chloride or bromide, an anhydride or mixed anhydride, e.g., with pivalic acid or formed with a haloformate, or an active ester or azide; alternatively, the acid itself can be used, together with an esterifying agent, e.g., carbonyldiimidazole or a carbodiimide such as N,N'-diethyl-, —dipropyl—, or —diisopropyl-carbodiimide, or preferably N,N'-dicyclohexyl-carbodiimide.

The acylation should be effected under such conditions that both lactone formation and $\Delta^3 \rightarrow \Delta^2$ isomerisation are substantially avoided. Lactone formation can be reduced by esterification of the 4-carboxy group before acylation. The esterifying group should be readily introducible and removable without resulting in $\Delta^3 \rightarrow \Delta^2$ isomerisation. As mentioned above preferred protecting groups are the diphenylmethyl group and the β,β,β-trichloroethyl group which can be readily introduced and removed (after acylation of the 3-CH$_2$OH group) substantially without $\Delta^3 \rightarrow \Delta^2$ isomerisation.

The esterifying group is preferably removed before the cephalesporanic acid derivative is reacted with the incoming nucleophile.

3-Haloacetoxymethyl-7β-acylamidoceph-3-em-4-carboxylic acids, the halogen atom(s) being chlorine bromine or iodine, and 3-formyloxymethyl-7β-acylamidoceph-3-em-4-carboxylic acids and salts thereof e.g. with alkali metals such as sodium or potassium and with organic bases, and esters thereof, where the esterifying group is preferably one which is readily introducible and removable without appreciable $\Delta^3 \rightarrow \Delta^2$ isomerisation, are novel compounds and constitute a further feature of the invention.

NITROGEN LEAVING-GROUPS

A further class of starting materials useful in the process according to the invention has the partial formula

Q—CH$_2$—N<

(where Q is as hereinbefore defined), a preferred group of compounds of this type being isothiocyanates having the formula

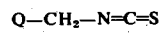
Q—CH$_2$—N=C=S

It is desirable that the 4-carboxy group should not be esterified but be present as COO$^-$ or COOH when X represents an oxygen or nitrogen leaving group.

INCOMING NUCLEOPHILES

NITROGEN NUCLEOPHILES

Examples of nitrogen nucleophiles include tertiary aliphatic, aromatic, araliphatic and cyclic amines including trialkylamines, for example, triethylamine, pyridine bases such as pyridine and alkyl pyridines; heterocyclic amines having more than one heteroatom, at least one heteroatom being nitrogen, such as pyrimidines, purines, pyridazines, pyrazines, pyrazoles, imidazoles, triazoles and thiazoles.

Thus the term "nitrogen nucleophile" includes compounds of the following formulae:

NR$^a$R$^b$R$^c$  (a)

in which R$^a$, R$^b$ and R$^c$, which may be the same or different are substituted or unsubstituted aliphatic, araliphatic or aromatic groups; any two together with the nitrogen atom if desired forming a heterocyclic ring which may be interrupted by one or more further heteroatoms;

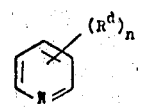
(b)

in which $n$ is 0 or an integer from 1 to 5 and $R^d$, which when $n$ is from 2 to 5, may be the same or different, is an aliphatic, aryl or araliphatic group or an alkoxy- or acyloxymethyl, formyl, carbamoyl, acyloxy, esterified carboxyl, alkoxy, aryloxy, aralkoxy, alkylthio, arylthio, aralkylthio, cyano, hydroxy, N-menoloweralkyl carbamoyl, N,N-diloweralkyl-carbamoyl, N-(hydroxyloweralkyl)carbamoyl, or carbamoylloweralkyl radical.

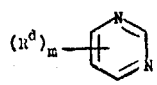  (c)

in which $R^d$ is as defined in (b) and $m$ is 0 or an interger from 1 to 4,

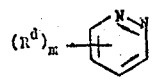  (d)

in which $R^d$ and $m$ are as defined in (c),

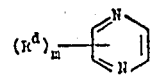  (e)

in which $R^d$ and $m$ are as defined in (c),

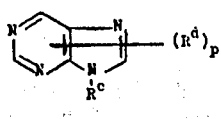  (f)

in which $R^d$ is as defined in (b), $p$ is 0 or an integer from 1 to 3, and $R^e$ is an aliphatic, araliphatic, aryl, or acyl radical or a hydrogen atom.

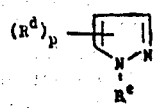  (c)

in which $R^d$, $R^e$ and $p$ are as defined in (f),

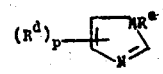  (h)

in which $R^d$, $R^e$ and $p$ are as defined in (f),

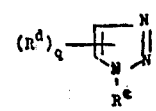  (i)

in which $R^d$ and $R^e$ are as defined in (f) and $q$ is 0, 1 or 2,

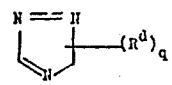  (j)

in which $R^d$ and $q$ are as defined in (i),

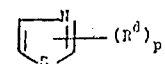  (k)

in which $R^d$ and $p$ are as defined in (f), and

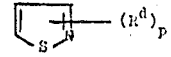  (l)

in which $R^d$ and $p$ are as defined in (f).

CARBON NUCLEOPHILES

Examples of "carbon nucleophiles" include cyanides, pyrroles and substituted pyrroles, e.g., indoles, and compounds giving stabilised carbanions, for example, acetylenes and compounds having 3-diketone groups, for example, acetoacetic and malonic esters and cyclohexane-1,3-diones.

Thus the term "carbon nucleophile" includes compounds of the following formulae:

  (a')

in which M is a metal cation, preferably an alkali metal or alkaline earth metal cation or a quaternary ammonium ion, and $v$ is the valency of the cation.

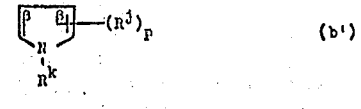  (b')

in which $R^j$ is an aliphatic, araliphatic or aryl group or an esterified carboxy, acyloxy or acyl group, $p$ is 0 or an integer from 1 to 3, and $R^k$ is an alkyl, aralkyl, or aryl group or a hydrogen atom, at least one of the β-positions being unsubstituted,

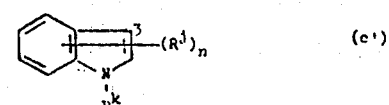  (c')

in which $R^j$ and $R^k$ are as defined in (b') and $n$ is 0 or an integer from 1 to 5, the 3-position being unsubstituted,

  (d')

in which $R^g$ is an aliphatic, araliphatic or aryl group or a hydrogen atom, and M and $v$ are as defined in (a').

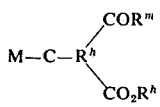  (e′)

in which the group $R^h$, which may be the same or different, are hydrogen atoms or alkyl, aralkyl or aryl groups and $R^m$ is an alkyl, aralkyl, aryl, alkoxy, aralkoxy or aryloxy group.

  (f′)

where R is an electron donating group or atom and $n$ is 0 or an integer of from 1 to 5.

SULPHUR NUCLEOPHILES

Examples of "sulphur nucleophiles" include thiourea and aliphatic, aromatic, araliphatic, alicylic and heterocyclic substituted thioureas, aromatic and aliphatic thioamides, for example thioacetamide and thiosemicarbazide, and thiosulphates.

Thus the term "sulphur nucleophile" includes compounds of the formulae:

  (a″)

in which $R^1$, $R^2$, $R^3$ and $R^8$, which may be the same or different, represent hydrogen atoms, aliphatic, alicyclic, aromatic, araliphatic or heterocyclic groups, or $R^1$ and $R^3$ together form a divalent group. $R^2$ or $R^8$ may alternatively be a group $-NR^1R^3$ where $R^1$ and $R^3$ are as defined above.

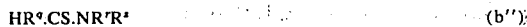  (b″)

in which $R^q$ is a straight or branched chain aliphatic or araliphatic group, and $R^r$ and $R^s$, which may be the same or different, are aliphatic, araliphatic, acyl or aryl groups or hydrogen atoms.

  (c″)

in which M is a metal cation, preferably an alkali or alkaline earth metal cation, or a quaternary ammonium ion, and $y$ is the valency of the cation.

OXYGEN NUCLEOPHILES

Examples of oxygen nucleophiles include water and alcohols, for example alkanols such as methanol, ethanol, propanol and butanol. Water furnishes both $H_2O$: and $OH^-$ and is thus a competitor nucleophile in any reaction occurring in aqueous medium.

The term "oxygen nucleophile" thus includes compounds of the following formula:

in which the group $R^t$ may be lower alkyl (e.g. methyl, ethyl, n-propyl, isopropyl, n-butyl, isobutyl etc.); lower alkenyl (e.g. vinyl, allyl, isopropenyl, etc.); lower alkynyl (e.g. ethynyl, propynyl, etc); lower cycloalkyl (e.g. cyclopentyl, cyclohexyl, etc); lower cycloalkyl lower alkyl (e.g. cyclopentylmethyl, cyclohexylethyl etc.); aryl (e.g. phenyl or naphthyl); aryl lower alkyl (e.g. benzyl); heterocyclic; heterocyclic lower alkyl (e.g. furfuryl) or any of these groups substituted by, for example, one or more of lower alkoxy (methoxy, eth-oxy, etc.); lower alkylthio (methylthio, ethylthio etc), halogen(chlorine, bromine, iodine or fluorine), lower alkyl (methyl, ethyl etc), nitro, hydroxy, acyloxy, carboxy, carbalkoxy, lower alkylcarbonyl, lower alkylsuphinyl, lower alkylsulphonyl, lower alkoxysulphonyl, amino, lower alkylamino or acylamino groups.

We particularly prefer those compounds in which the group $R^t$ is a lower alkyl group. These 7β-acylamido-3-loweralkoxymethyl-ceph-3-em-4-carboxylic acids have shown interesting properties as orally administrable antibiotics as is described in copending Application No. 752,191 filed on even date, now Pat. No. 3,665,003.

REACTION CONDITIONS

The reaction may conveniently be effected by maintaining the reactants in solution at a moderate temperature, e.g., 0°–120°C., preferably 35°–75°C, advantageously about 50°C. Reactions are usually complete (in aqueous solvents) in about 15 min at 50°, and in correspondingly longer times at lower temperatures or correspondingly shorter times at higher temperatures. The reaction is advantageously effected using from one molar equivalent to ten molar equivalents of incoming nucleophile. The pH value of the reaction solution under aqueous conditions is advantageously maintained within the limits 5 – 8, preferably 6 – 7. If necessary the pH of the solution should be adjusted to the desired value by the addition of a buffering agent such as sodium acetate. When working under non-aqueous conditions, the reaction medium should be neither extremely basic nor extremely acidic.

Since the reaction appears to proceed by a polar or ionic mechanism it is desirable to employ a polar medium for the reaction to proceed. The most generally suitable is water but organic solvents such as dioxan, ethyl acetate, formamide, N,N-dimethylformamide or acetone may be employed. The organic solvents may be used in the presence or absence of water.

Where essentially non-aqueous conditions are used the alcohol or phenol may itself be used as the reaction medium and this is advantageous in that the absence of water from the reaction medium precludes a competitive reaction between the water and the cephalosporin molecule taking place. Non-polar solvents may also be used, in which cases the addition of as little 0.5% of water will often bring about the desired amount of polarity. In certain cases the nucleophile itself may be the solvent, particularly when the ethers are being prepared from alcohols.

Organic media which may be used include lower alkanoic acid nitriles e.g. acetonitrile or propionitrile; halogenated hydrocarbons e.g. methylene chloride, carbon tetrachloride, chloroform, ethylene dichloride or perchloroethylene, lower nitrealkanes, e.g. nitromethane; nitro-aromatic compounds. e.g. nitrobenzene cyclic ethers e.g. dioxan or tetrahydrofuran amides of the general formula $R^5.CO.NR^6R^7$ where $R^5$ is a hydrogen atom or an alkyl group containing 1 to 5 carbon atoms and $R^6$ and $R^7$, which may be the same or different, are each a hydrogen atom or an alkyl group containing 1 to 5 carbon atoms, or, alternatively $R^6$ and $R^7$ together form a divalent aliphatic group which, together with the adjacent nitrogen atom, forms a heterocyclic ring. Examples of amides of this type are N,N-dimethylformamide, N,N-diethylformamide, N,N-dimethylacetamide, formamide and N-methylformamide. Other solvents which may be used include N-lower alkyl pyrrolidones e.g. N-methylpyrrolidene and di-lower alkyl sulphoxides, e.g. dimethylsulphoxide.

The reaction medium need not be liquid at room temperature. Solids, e.g. acetamide, may be used so long as they are liquid at the reaction temperature.

The reaction product may be separated from the reaction mixture, which may contain, for example, unchanged cephalosporin and other substances, by a variety of processes including recrystallization, ionophoresis, paper chromatography or by chromatography on ion exchange resins.

ACYL GROUPS

Whilst R may represent an acyl group in general terms, one may use specific acyl radicals as defined in the following general formulae, but it should, however, be noted that this is not intended to be an exhaustive list of all the possible N-acyl groups which may be present.

i. $R^uC_nH_{2n}CO$ — where $R^u$ is aryl(carbocyclic or heterocyclic), cycloalkyl, substituted aryl, substituted cycloalkyl, or a non-aromatic heterocyclic group, and $n$ is an integer from 1 – 4. Example of this group include phenylacetyl, substituted phenylacetyl, e.g., fluorophenyl-acetyl, nitrophenylacetyl, acetoxyphenylacetyl, alkanoyl-phenylacetyl, or hydroxyphenylacetyl, thienyl-2— and —3-acetyl, 4-isoxazolyl- and substituted 4-isoxazolyl-acetyl and pyridylacetyl.

The substituted 4-isoxazolyl group may be a 3-aryl-5-methyl-isoxazol-4-yl group, the aryl group being e.g. phenyl or halophenyl, e.g., chloro- or bromo- phenyl. An acyl group of this type is 3-o-chlorophenyl-5-methyl-isoxazol-4-acetyl.

ii. $C_nH_{2n+1}.CO$— where $n$ is an integer from 1 – 7. The alkyl group may be straight or branched, and if desired, may be interrupted by an oxygen or a sulphur atom or substituted by e.g. a cyano group. Examples of such groups include hexanoyl, heptanoyl, octanoyl, butylthioacetyl, and cyanoacetyl.

iii. $C_nH_{2n-1}CO$ — where $n$ is an integer from 2 – 7. The alkenyl group may be straight or branched and, if desired, may be interrupted by an oxygen or a sulphur atom. Examples of such groups include acrylyl, crotonyl and allylthioacetyl.

iv. $R^uO.CH_2.CO$ — where $R^u$ has the meaning defined under (i). An example of such a group is phenoxyacetyl.

v. $R^uSCH_2.CO$ — where $R^u$ has the meaning defined above. Examples of such thio groups include S-phenylthioacetyl, S-chlorophenylthioacetyl and S-bromophenylthioacetyl.

vi. $R^u(CH_2)_nZ(CH_2)_m.CO$ — where $R^u$ has the meaning defined above, $m$ is an integer from 1-5, $n$ is an integer from 1–4, and Z is an oxygen or sulphur atom. Examples of such groups include S-benzylthioacetyl, S—benzylthiopropionyl and S-phenethylthioacetyl.

vii. $R^uCO$ — where $R^u$ has the meaning defined above. Examples of such groups include benzoyl, substituted benzoyl (e.g., aminobenzoyl), 4-isoxazolyl- and substituted 4-isoxazolyl-carbonyl, and cyclopentanecarbonyl. Where the benzoyl group is substituted the substituents may for example be alkyl or alkoxy and may be in the 2- or 2-and 6-positions; an example of such a group is 2,6-dimethoxybenzoyl. Where the group $R^u$ represents a substituted 4-isoxazolyl group, the substituents may be as set out under (i) above. An acyl group of this type is 3-o-chlorophenyl-5-methyl-isoxazol-4-yl-carbonyl.

viii. Amino acyl, for example $R^uCH(NH_2).(CH_2)_nCO$ where $n$ is an integer from 1-10, or $NH_2.Ar(CH_2)_mCO$ where $m$ is zero or an integer of from 1-10, $R^w$ is a hydrogen atom or an alkyl, aralkyl or carboxy group or a group as defined under $R^u$ above, and Ar is an arylene group, e.g. p-phenylene or 1,4-naphthylene. Examples of such groups are disclosed in British Patent Specification No. 1,054,806. A group of this type is the p-aminophenylacetyl group. Other acyl groups of this type include those, e.g. δ-aminoadipoyl, derived from naturally occurring amino acids.

(ix) 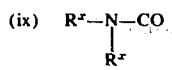

where the groups $R^x$, which may be the same or different, are hydrogen atoms or monovalent organic groups, e.g., lower alkyl or halogen substituted lower alkyl.

x. Glyoxylyl and substituted glyoxylyl groups of the formula $R^y.CO.CO$ — where $R^y$ is an aliphatic, araliphatic or aromatic group, e.g. an aromatic group having an atomic weight sum greater than 78, e.g., a thienyl group or a mono-, di-, or tri-substituted phenyl group, the substituents being, for example, one or more halogen atoms (F, Cl, Br or I), methoxy groups, methyl groups or amino groups, or a fused benzene ring. Included in this group are also the α-carbonyl derivatives of the above glyoxylyl and substituted glyoxylyl groups, formed for example with hydroxylamine, semicarbazide, thiosemicarbazide, isoniazide or hydrazine.

xi. α-Substituted carboxylic acid acyl groups, where the α-substituent is an amino, substituted amino [e.g. acylamido or a group obtained by reacting the amino group and/or acylamido group(s) with an aldehyde or ketone e.g. acetone or methyl ethyl ketone], hydroxy, carboxy, esterified carboxy, cyano, halogeno, acyloxy (e.g. formyloxy or lower alkanoyloxy) or etherified hydroxy group. The carboxylic acid may be aliphatic, e.g., an α-substituted parafiinic acid, or araliphatic, e.g., an α-substituted phenylacetic acid. Acyl groups of this character include the group Ar CH(X)CO where Ar and X have the meanings defined below.

The following Examples illustrate the invention. In the Examples:

System A is descending n-propanol-water = 73, on Whatman No. 1 Paper at room temperature.

System B is butanolethanol:water = 4:1:5, equilibrated at room temperature, the upper phase being used as developer in descending manner, in equilibrium with lower phase, on Whatman 3MM paper buffered to pH6 with 0.05M sodium dihydrogen phosphate.

System C is ethyl acetate:butanol0.1M-sodium acetate, pH15 = 8:1:8, equilibrated at 38°C, the upper phase being used as developer in descending manner, in equilibrium with lower phase at 38°, on No. 1 Whatman paper buffered to pH5 with 0.1M sodium acetate.

$R_T$ represents the $R_F$ value divided by that of 3-acetoxymethyl-7β-(2'-thienylacetamido)ceph-3-em-4-carboxylic acid.

The conditions for electrophoresis are those described by Cocker et al., J. Chem. Soc. 1965, 5015.

Organic solutions were dried over desiccated magnesium sulphate.

Cephaloridine was detected by the blue colour it gave with the potassium iodoplatinate spray reagent described in "Chromatography", E. Merck A. G., Darmstadt, page 133.

EXAMPLE 1

Preparation of N-[7β-(2'-thienylacetamide)-ceph-3-em-4-ylmethyl]-pyridinium-4-carboxylate The title compound was prepared via the following reaction scheme (the steps are described in more detail below)

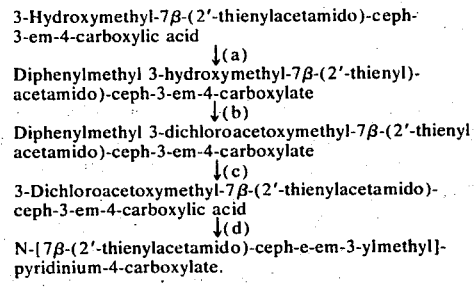

a. Diphenylmethyl 3-hydroxymethyl-7β-(2'-thienylacetamido)-ceph-3-em-4-carboxylate 3-Hydroxymethyl-7β-(2'-thienylacetamido)ceph-3-em-4-carboxylic acid (500 mg.) was dissolved in dry tetrahydrofuran and treated with a solution of diphenyldiazomethane (300 mg., 1.1 equiv.) in petrol. Nitrogen was evolved slowly, and after 2½ hours the solution was evaporated, the residue dissolved in ethyl acetate, and the solution was washed with bicarbonate solution and re-evaporated. This gave a gum which solidified on trituration with ether (0.5 g.). A sample was recrystallised from methanol, m.p. 164°, $[\alpha]_D^{23}=$ +25° (c, 1.0, dioxan), +22° (c 1.0, tetrahydrofuran). $\lambda\lambda_{max}$. ethanol 234 nm. $E_{1\ cm}^{1\%} = 255$, ($\epsilon = 13,300$), 259 nm. $E_{1cm}^{1\%} = 151$ ($\epsilon$ 7,850), $\nu_{max}$. (bromoform) 3420 (OH), 3280 (NH), 1750 (β-lactam), 1722 cm$^{-1}$ (COOR). (Found, C, 62.2; H, 4.5; N, 5.4; S, 12.1. $C_{27}H_{24}N_2O_5S_2$ requires C, 62.3; H, 4.7; N, 5.4; S, 12.3%) $R_F = 0.83$ (Kieselgel G plates; ethyl acetate:-benzene=1:2).

b. Diphenylmethyl 3-dichloroacetoxymethyl-7β-(2'-thienylacetamido)-ceph-3-em-4-carboxylate Diphenylmethyl 3-hydroxymethyl-7β-(2'-thienylacetamido) ceph-3-em-4-carboxylate (2.08 g., 4 mmole.) and pyridine (1.58 ml.; 20 mmole) were dissolved in dry tetrahydrofuran (100 ml.) and cooled to −20°. Dichloroacetyl chloride (2.95 g; 1.96 ml; 20 mmole.) in dry tetrahydrofuran (5 ml) was added dropwise. 15 minutes after the addition the mixture was filtered and evaporated, and the residue was partitioned between ethyl acetate and sodium bicarbonate solution. The organic layer was washed with brine, dried and taken to small volume; this solution was then added dropwise to petrol to give a white solid (2.1 g; 85%), m.p. >60° (softens), $[\alpha]_D^{23} = +17.5°$ (c 1.14, dioxan), $\lambda\lambda_{max}$(ethanol) 236nm ($\epsilon = 13,300$), 259nm ($\epsilon = 7,600$), $\nu_{max}$(CHBr$_3$) 1783 (β-lactam), 1760 (CO$_2$CHCl$_2$), 1725 (COOR), 1680 and 1510 cm$^{-1}$ (CONH). N.M.R. spectrum (CDCl$_3$) —COCHCl$_2$ 4.13τ, $R_F = 0.37$ (Kieselgel G plate; benzene:ethyl acetate = 5:1).

c. 3-Dichloroacetoxymethyl-7β-(2'-thienylacetamide) ceph-3-em-4-carboxylic acid Diphenylmethyl 3-dichloroacetoxymethyl-7β-(2'-thienyl-acetamido)ceph-3-em-4-carboxylate (6.8 g.) was dissolved in anisole (5 ml.), and trifluoroacetic acid (15 ml.) was added. After 4 minutes the solvent was removed at 30°. The residue was dissolved in ethyl acetate and re-evaporated; the gum was redissolved in ethyl acetate (10 ml.) and added dropwise, with stirring, to petroleum ether (400 ml.). The product was obtained as a yellow solid, m.p. >60° (softens; decomp. at 99°) (4.92 g.; 95%), $[\alpha]_D^{27}= +56°$ (c, 0.7; dioxan), $\lambda\lambda_{max}$.(ethanol) 237nm ($\epsilon$=12,500), 259nm ($\epsilon$ = 7,500), $\nu_{max}$(CHBr$_3$) 3390 (NH), 1788 (β-lactam), 1760 (COOR), 1685 and 1518 (CONH), 1735 and 1715 cm$^{-1}$ (COOH). N.M.R. spectrum (CDCl$_3$) —O.-COCHCl$_2$ 4.0τ.

The dicyclohexylamine salt crystallised from acetone, m.p. >100° (softens; decomp. at 210°). $[\alpha]_D^{25}= +36°$ (c 1.0, chloroform), $\lambda\lambda_{max}$ (ethanol) 235nm ($\epsilon$ = 13,600), 265 nm ($\epsilon$ =6,950), $\nu_{max}$(CHBr$_3$) 1774 (β-lactam), 1765 (COOR), 1635 (COO$^-$), 1680 and 1518 (CONH), 812 cm$^{-1}$ (CHCl$_2$). N.M.R. spectrum (CDCl$_3$) - CH$_2$.O.COCHCl$_2$ 3.91τ. (Found C, 52.0; H, 5.7; N, 6.3; Cl, 14.2. $C_{16}H_{14}Cl_2N_2O_6S_2$. $(C_6H_{11})_2$NH requires C, 52.0; H, 5.8; N, 6.5; Cl, 14.8%).

d. Reaction of 3-dichloroacetoxymethyl-7β-(2'-thienylacetamido)-ceph-3-em-4-carboxylic acid with pyridine This reaction was shown to proceed in dioxan, ethyl acetate, methanol, dimethylformamide, formamide and water to give cephaloridine. With the assay procedure described by Taylor (J. Chem. Soc., 1965, 7020), the reaction appeared to give the highest yields in those solvents of high dielectric constant.

| Solvent | Dielectric Constant at 25°C | Maximum Yield (%) |
|---|---|---|
| Dioxan | 2.2 | 10 |
| Ethyl acetate | 6.0 | 3 |
| Methanol | 32.6 | 21 |
| N,N-Dimethylformamide | 36.7 | 20 |
| Formamide | 100 | 53 |
| Water | 78.5 | 44 |

The reaction was shown to proceed at temperatures between 25° and 75°. It was also shown that the reaction proceeded with increased efficiency in the non-polar solvents as the percentage of water in these solvents was increased.

The reaction was most efficient when 2 equivalents of pyridine were employed.

EXAMPLE 2

Preparation of N-[7β-(2'-thienylacetamido)ceph-3-em-4-ylmethyl]-pyridinium-4-carboxylate The title compound was prepared via the following reaction scheme (the steps are described in more detail below)

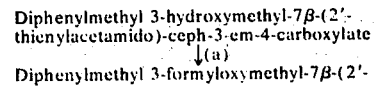

-continued thienylacetamido)-ceph-3-em-4-carboxylate
↓(b)
3-Formyloxymethyl-7β-(2'-thienylacetamido)-ceph-3-em-4-carboxylic acid
↓(c)
N-[7β-(2'-thienylacetamido)-ceph-3-em-3-ylmethyl]-pyridinium-4-carboxylate.

a. Diphenylmethyl 3-formyloxymethyl-7β-(2'-thienylacetamido)-ceph-3-em-4-carboxylate Diphenylmethyl 3-hydroxymethyl-7β-(2'-thienylacetamido)-ceph-3-em-4-carboxylate (3 g., 5.8 mmole.) and pyridine (6.5 ml., 82 mmole.) were dissolved in dry tetrahydrofuran (100 ml.), and cooled to −60°. A solution of formyl fluoride (~80 mmole.) in dry tetrahydrofuran (100 ml.), and cooled to −60°. A solution of formyl fluoride (80 mmole.) in dry tetrahydrofuran was added dropwise and the mixture maintained at −40° for 1 hour. On reaching room temperature, the mixture was filtered, concentrated, and partitioned between ethyl acetate and 2N-hydrochloric acid. On washing with more acid the ethyl acetate solution precipitated some product (1.77 g.); the remaining ethyl acetate was dried and evaporated to give more product (1.32 g.). A sample of the product was recrystallised from ethyl acetate, m.p. 189°, $\nu_{max}$ (CHBr$_3$), 1792 (β-lactam), 1730 and 1232 (COOR), 1690 and 1518 cm$^{-1}$ (CONH). N.M.R. spectrum (dimethylsulphoxide) CHO at 179τ. (Found: C, 61.7; H, 4.4; N, 4.8. $C_{28}H_{24}H_2O_6S_2$ requires C, 61.3; H, 4.4; N, 5.1%) $N_F$ = 0.7 (Kieselgel G plate, benzene:ethyl acetate = 2:1).

b. 3-Formyloxymethyl-7β-(2'-thieny acetamido)ceph-3-em-4-carboxylic acid

Diphenylmethyl 3-formyloxymethyl-7β-(2'-thienylacetamido)ceph-3-em-4-carboxylate (1.5 g.) was suspended in anisole (5 ml.), and trifluoroacetic acid (10 ml.) was added. After 4 minutes the mixture was evaporated to dryness at 0.1 mm. The residual solid was washed with ether to give the title compound (960 mg., 91%). A sample was recrystallised from methanol-petrol, m.p. >90° (softens; decomp. at 107°), $\lambda\lambda_{max}$ (pH6-phosphate buffer) 233nm (ε = 13,200), 260 nm (ε = 6,800). Found: C, 46.5; H, 3.9; N, 6.5; S, 16.0, $C_{15}H_{14}N_2O_6S_2$.½H$_2$O requires C, 46.1; H, 3.8; N, 6.9; S, 16.3%.

Sodium salt: $\lambda\lambda_{max}$ (pH6-phosphate buffer) 232nm (ε = 13,000), 257-9 nm (ε = 6,300), $\nu_{max}$(Nujol) 1752 (β-lactam), 1718 and 1170 (formate), 1608 (CCO$^-$), 1660 and 1538 cm$^{-1}$ (CONH). N.M.R. spectrum (D$_2$O), $^-$CHO at 1.8τ, $R_T$ = 0.7 (System C). Found C, 46.5; H, 3.9; N, 6.5; S, 16.02, $C_{15}H_{14}N_2C_6S_2$.½H$_2$O requires C, 46.1; H, 3.8; N, 6.9; S, 16.3%.

c. N-[7β-(2'-thienylacetamido)-ceph-3-em-3-ylmethyl]-pyridinium-4-carboxylate 3-Formyloxymethyl-7β-(2'-thienylacetamido)-ceph-3-em-4-carboxylic acid (38 mg.) was kept at 38° in water (1 ml.) containing pyridine (0.08 ml.). After 1, 2, and 3 hours, aliquots (5 μl) were subjected to electrophoresis at pH 1.9 and to paper chromatography in system C. The formation of cephaloridine was established by comparison with a standard spot of cephaloridine on the electrophoretograms and chromatograms, and by spraying the papers with iodoplatinate reagent, which gives a blue colour with cephaloridine.

EXAMPLE 3

Reaction of 3-acetoxy-, 3-chloroacetoxy-, 3-dichloroacetoxy-, 3-trichloroacetoxy- and 3-phenylglyoxylyloxy-methyl-7β-(2'-thienylacetamido)ceph-3-em-4-carboxylic acids with (a) aqueous base and (b) aqueous pyridine The 3-chloroacetoxymethyl, 3-trichloroacetoxymethyl and 3-phenylglyoxylyloxymethyl- compounds were prepared by adding pyridine (4 equivalents), or a solution of pyridine (4 eqivalents) in dry peroxide-free tetrahydrofuran dropwise with stirring at room temperature to a solution of diphenylmethyl 3-hydroxymethyl-7β-(2'-thienylacetamido)ceph-3-em-4-carboxylate and the appropriate acid chloride (4 equivalents) in dry peroxide-free tetrahydrofuran. The mixture was stirred for 30 minutes; the precipitated pyridine hydrochloride was removed and the filtrate evaporated to dryness. The residue was dissolved in ethyl acetate and the solution washed with saturated sodium bicarbonate solution to remove unreacted acid chloride. Further washing with dilute hydrochloric acid and brine was carried out before the solution was dried (MgSO$_4$) and evaporated. If the residue could not be induced to crystallise, it was dissolved in ethyl acetate and the product was obtained in solid form by slowly adding this solution to a large volume of petroleum ether.

In a manner analogous to that described in Example 1(c) the diphenylmethyl esterifying group was removed by acid hydrolysis using trifluoroacetic acid in conjunction with anisole.

a. 3-Acetoxymethyl-7β-(2'-thienylacetamido)ceph-3-em-4-carboxylic acid was dissolved in aqueous 0.5N-sodium bicarbonate; it remained unchanged. However, the remaining compounds in the title were instantaneously converted under the same conditions into products with the same $R_F$ values as 3-hydroxymethyl-7β-(2'-thienylacetamido)ceph-3-em-4-carboxylic acid.

b. The compounds described in the title (38 mg.) were each kept at 38° in water (1 ml.) containing pyridine (0.08 ml.). After 1, 2, and 3 hours, aliquots (5 μl) were subjected to electrophoresis at pH 1.9 and to paper chromatography in system C. The formation of cephaloridine was established by comparison with a standard spot of cephaloridine on the electrophoretograms and chromatograms, and by spraying the papers with iodoplatinate reagent, which gives a blue colour with cephaloridine.

After 3 hours there was only a trace of cephaloridine produced from 3-acetoxymethyl-7β-(2'-thienylacetamido)ceph-3-em-4-carboxylic acid, but with all of the other compounds conversion to cephaloridine was complete in 1 hour and appeared to be efficient.

EXAMPLE 4

Preparation of cephaloridine

3-Dichloroacetoxymethyl-7β-(2'-thienylacetamido)-ceph-3-em-4-carboxylic acid (0.1 g., 2.15 mmole.) was suspended in water (4 ml.), and pyridine (0.352 ml., 4.3 mmole.) was added. The solution was heated at 50° for 1 hour, acidified to pH 4.5 with acetic acid, and washed with ethyl acetate and finally with petrol. The aqueous solution was freed from dissolved organic solvents and applied to a column comprising (from top to bottom) layers of deactivated neutral alumina (8 ml.), Dowex 1 (AcO⁻) (20 ml.) and Zeokarb 226 (H⁺) (5 ml.). Elution with water was carried out until the eluate showed no optical rotation; the total eluate was freeze-dried and the residue triturated with methanol to give a white solid (296 mg.), $[\alpha]_D^{23}$ +48.8° (c 0.8, water), $\lambda\lambda_{max}$(water) 238nm ($E_{1cm}^{1\%}$ = 351), 255 nm ($E_{1cm}^{1\%}$ = 324).

The product had an infrared and N.M.R. spectrum identical with authentic cephaloridine. It also had identical chromatographic and electrophoretic behaviour.

EXAMPLE 5 a. 3-Isothiocyanatomethyl-7β-(2'-thienylacetamido)ceph-3-em-4-carboxylic acid.

3-Dichloroacetoxymethyl-7β-(2'-thienylacetamido)-ceph-3-em-4-carboxylic acid (2 g.) was dissolved in acetone (30 ml.) containing water (0.3 ml.), and potassium thiocyananate (2 g.) was added. The mixture was kept at 47° for 30 minutes and then poured into 2N-hydrochloric acid (20 ml.). The product was extracted into ethyl acetate; washing with saturated sodium bicarbonate solution transferred the product to the aqueous layer, from which it was isolated by acidification and extraction into ethyl acetate. The organic layer was dried and concentrated and the solution then poured into stirred petrol; the product separated as a pale yellow solid (600 mg.). Of this solid, 500 mg. was dissolved in acetone and treated with sodium 2-ethyl-hexanoate solution (1.1 equiv.); on addition of ether, the sodium salt of the title compound precipitated. This salt was dissolved in water and filtered through neutral alumina, and the eluate was freeze-dried to give a white solid (400 mg.), $[\alpha]_D^{25}$ = +29° (c 1.0, water), $\lambda\lambda_{max}$ (pH6 phosphate buffer) 236nm ($\epsilon$ = 14,200), 260nm ($\epsilon$ = 8,600), $\nu_{max}$ (of the acid) (CHBr₃) 2090 (N=C=S), 1790 (β-lactam), 1730 (COOH), 1682 and 1518 cm⁻¹ (CONH). N.M.R. spectrum (D₂O) C$\underline{H}$ ₂-N=C=S at 5.50τ. (Found: C, 39.3; H, 3.3; N, 8.4. C₁₅H₁₂N₃O₄S₃Na.2½H₂O requires C, 39.0; H, 3.7; N, 9.0%) R$_T$ = 2.05 (system C), 1.35 (system B). The product reacted in dimethylformamide with sodium azide, evolving a gas, so probably confirming the presence of an isothiocyanate group. (Lieber, Chem, and Ind., 1958, 1234).

b. Reaction of 3-isothiocyanatomethyl-7β-(2'-thienylacetamido)-ceph-3-em-4-carboxylate acid with pyridine The isothiocyanate (5 mg.) in water (0.4 ml.) containing pyridine (0.08 ml.) was kept at 50° for 1 hour. An aliquot of the reaction mixture was subjected to electrophoresis at pH 1.9 and to paper chromatography and shown to contain a component which had the same migration and chromatographic behaviour as cephaloridine.

EXAMPLE 6

N-[7β-(2'-Thienylacetamide)ceph-3-em-3-ylmethyl]-triethylammonium-4-carboxylate

3-Dichloroacetoxymethyl-7β-(2'-thienylacetamido)-ceph-3-em-4-carboxylic acid (1 g.) was dissolved in wateracetone (0.5:99.5) (10 ml.), and triethylamine (0.55 ml: 2 equivs) was added. The mixture was kept at room temperature for 30 minutes and then poured into ethyl acetate; water and acetic acid were added simultaneously so that the pH did not exceed 4.0. The aqueous solution, after washing with ethyl acetate, was passed through a Dowex 1 (AcO⁻) column and the eluate freeze-dried. The lyophilised solid was dissolved in methanol and precipitated by pouring this solution into ether. This gave a white solid (130 mg.), $[\alpha]_D^{23}$ = +93° (c. 1.15, water), $\lambda\lambda_{max}$(water 237 nm ($\epsilon$ = 12,600), 260nm ($\epsilon$ = 9,000) N.M.R. spectrum (D₂O)-CH₂N⁺(C$\underline{H}$₂.C$\underline{H}$₃)₃ systems centred at 6.73 and 8.72τ. (Found: C, 49.0, H, 6.9; N, 9.2. C₂₀H₂₇N₃O₄S₂.3H₂O requires C, 48.9; H, 6.7; N, 8.6%). On electrophoresis at pH 7.0 the compound showed no nettcharge, and at pH 1.9 it moved less than cephaloridine. The compound stained blue with iodeplatinate reagent.

EXAMPLE 7

3-Ethoxymethyl-7β-(2'-thienylacetamido)ceph-3-em-4-carboxylic acid

3-Dichloroacetoxymethyl-7β-(2'-thienylacetamido)-ceph-3-em-4-carboxylic acid (4.74 g.) was refluxed in ethanol (175 ml.) for 60 minutes; the mixture was filtered and the filtrate evaporated to give an oil. Trituration with ethyl acetate gave a solid (354 mg.), which was discarded. The ethyl acetate solution was extracted with sodium bicarbonate solution; the aqueous layer was then acidified and extracted with ethyl acetate. On drying and evaporation this solution gave a gum (3.34 g.), which was redissolved in hot ethyl acetate. Addition of a fourfold volume of ether gave a solid, which was discarded. The filtrate was concentrated and set aside at 0°; a white solid (548 mg.) crystallised out, m.p. 160°–165° (decomp.), $[\alpha]_D^{25}$ = 157° (c 0.7, tetrahydrofuran) $\lambda\lambda_{max}$ (NaHCO₃ solution) 237nm ($\epsilon$ = 12,800), 260nm ($\epsilon$ = 8,000), $\nu_{max}$ (CHBr₃) 1770 (β-lactam), 1720 (COOH), 1659 and 1678 cm⁻¹ (CONH). N.M.R. spectrum (D₂O, with sodium bicarbonate) -O-C$\underline{H}$₂.C$\underline{H}$₃ systems centred at 6.5 and 8.83τ. (Found: C, 50.6; H, 4.8; N, 7.1; S, 16.3. C₁₆H₁₈N₂O₅S₂ requires C, 50.2; H, 4.7; N, 7.4; S, 16.8%). R$_F$ = 1.5 (System C), 1.35 (System B).

EXAMPLE 8

Preparation of 3-Ethoxymethyl-7β-(2'-thienylacetamido)-ceph-3-em-4-carboxylic acid a. Diphenylmethyl 3-chloromethyl-7β-(2'-thienylacetamido)ceph-3-em-4-carboxylate Diphenylmethyl 3-hydroxymethyl-7β-(2'-thienylacetamido) ceph-3-em-4-carboxylate (5.2 g., 10 mmole) and pyridine (4 ml., 40 mmole) in dry tetrahydrofuran (75 ml.) were added dropwise at 20° to a solution of thionyl chloride (2.38 g., 1.45 ml.; 20 mmole) in dry tetrahydrofuran (25 ml.) during one hour. After 15 minutes the mixture was poured into brine and the product extracted into ethyl acetate; the organic exract was dried and concentrated. The concentrate was added dropwise to petroleum ether (b.p. 40°–60°) and the solid product (3.9 g., 73%) was collected. A sample was recrystallised from ethanol, m.p. 125°–133° (decomp) $[\alpha]_D^{23}$ = 6.5° (c, 1.0, tetrahydrofuran); $\lambda\lambda_{max}$ (ethanol) 235 nm. ($\epsilon$ 13,200), 266 nm. ($\epsilon$ 8,000); $\nu_{max}$ (bromoform) 3390 (NH), 1785 (β-lactam), 1725 (COOR), 1682 and 1510 cm⁻¹ (CONH); τ (CDCl₃) 5.63, 3-methylene group singlet; (Found: C, 60.7; H, 4.7; N, 4.7; S, 11.7; Cl, 6.2; C₂₇H₂₃N₂O₄S₂ Cl requires C, 60.2; H, 4.3; N, 5.2; S, 11.9; Cl, 6.6%); $R_F$ = 0.47 (Silica plates, benzene:ethyl acetate = 5:1).

The active experiment was repeated using n-butyl chlorosulphite or dimethylaminochlorosulphite instead of thionyl chloride, the pyridine being added dropwise to the other reagents at −40°C. After complete addition of the pyridine, the mixture was allowed to warm to room temperature, poured into saturated brine, and worked up as above.

b.

3-Ethoxymethyl-7β-(2'-thienylacetamide)ceph-3-em-4-carboxylic acid

Diphenylmethyl 3-chloromethyl-7β-(2'-thienylacetamide) ceph-3-em-4-carboxylate (10.3 g.) was dissolved in ethanol (250 ml.) and kept at 60° for 4½ hours. The mixture was evaporated to give a froth (11.6 g.), which was dissolved in anisole (20 ml.) and treated with trifluoroacetic acid (70 ml.) for 6 minutes. The solvent was reacted at 40°/1 mm. The residual gum was triturated with ethyl acetate; the solid so obtained was discarded. The ethyl acetate solution was extracted with sodium bicarbonate solution, and the separated aqueous layer was acidified to pH 2.5 with phosphoric acid, and re-extracted with ethyl acetate. Drying and evaporation gave a gum which was taken up in the minimum amount of ethyl acetate, and a fourfold volume of ether was added. The precipitate was discarded and the filtrate evaporated to give a gum (2.0 g.) which was recrystallised from ethyl acetate to give the title compound (140 mg.). The mother liquor was concentrated and cooled to give a second impure crop of product (729 mg.). The product had the same $R_F$ values as the title compound.

EXAMPLE 9

3-n-Propoxymethyl-7β-(2'-thienylacetamido)-ceph-3-em-4-carboxylic acid

3-Dichloroacetoxymethyl-7β-(2'-thienylacetamido)-ceph-3-em-4-carboxylic acid (5 g., 12.9 mmoles) was refluxed in n-propanol (50 ml.) for 20 minutes. The solution was cooled and the precipitated brown solid was filtered off and discarded. The filtrate was treated with water (300 ml.) and the pH adjusted to 8.5 with aqueous sodium bicarbonate. The solution was extracted with ethyl acetate (2 × 20 ml.) and the extracts were discarded. The aqueous phase was acidified to pH 1.5 and extracted with ethyl acetate (3 × 20 ml.). After drying, the solution was removed and the residue dissolved in ethyl acetate (50 ml.), and ether (100 ml.) was added. The precipitated brown solid was filtered off and discarded, and the filtrate evaporated to dryness. The residue was twice recrystallised from aqueous ethanol to give the title compound as colourless needles (500 mg., 11.7%), m.p. 152°–154° (decomp) $[\alpha]_D^{25} = 79.8°$ (c 1.0, tetrahydrofuran), $\lambda_{max}$ (pH6-phosphate buffer) 236 nm. (ε = 13,600), 260 nm. (ε = 8,700) (shoulder), $\nu_{max}$(Nujol) 3310 (—NH—), 1772 (β-lactam), 1724 (—COOH), 1665 and 1535 cm$^{-1}$ (—CONH—). (Found: C, 51.3; H, 5.1; N, 6.9; S, 15.9. $C_{17}H_{20}N_2S_2O_5$ requires: C, 51.5; H, 5.1; N, 7.1; S, 16.2%). N.M.R. ($D_2O$-NaHCO$_3$) 5.78, 6.60, 8.52, 9.13τ (—CH$_2$OCH$_2$CH$_2$CH$_3$), $R_f$ 0.48 (System B); 0.54 (System C).

EXAMPLE 10

The reaction between 3-dichloroacetoxymethyl-7β-(2'-thienylacetamido)-ceph-3-em-4-carboxylic acid and various alcohols A solution of the title compound (0.25 g.) in the appropriate alcohol (10 ml.) was refluxed for 20 minutes. 10 μl. samples were taken and chromatographed in Systems B and C. The papers were viewed under ultraviolet light (254 nm). The $R_f$ values of the 3-alkoxymethyl) compounds produced are given below:

| Alcohol | $R_f$ System B | $R_f$ System C |
|---|---|---|
| CH$_3$OH | 0.26 | 0.29 |
| CH$_3$CH$_2$CH$_2$CH$_2$OH | 0.46 | 0.50 |

EXAMPLE 11

3-Isopropoxymethyl-7β-(2'-thienylacetamido)ceph-3-em-4-carboxylic acid

3-Dichloroacetoxymethyl-7β-(2'-thienylacetamido)-ceph-3-em-4-carboxylic acid (12.0 g., 25.8 m.mole.) was refluxed in isopropanol (100 ml.) for 45 minutes. After filtration through a pad of Kieselguhr, the isopropanol solution was poured into water (1000 ml.) and the pH adjusted to 8.5. The solution was extracted with ethyl acetate (2 × 100 ml.) and the extracts discarded. The solution was then acidified to pH 1.5 with 2N-hydrochloric acid and extracted with ethyl acetate (3 × 100 ml.). The ethyl acetate extracts were dried over magnesium sulphate and evaporated. The residue (8.5 g.) was dissolved in a mimimum of hot ethanol, from which the title compound separated on cooling (1.5 g., 15%). This material recrystallised from ethanol as colourless prisms, m.p. 169°–171° (d), $[\alpha]_D^{28}$+ 87° (c 1.0, tetrahydrofuran), $\lambda\lambda_{max}$ (ethanol) 237 nm (ε 14,500), 260 nm (ε 7,900), $\nu_{max}$ (Nujol) 1775 (β-lactam), 1728 (COOH), 1668 and 1535 cm.$^{-1}$ (CONH), N.M.R. (D$_2$O, with sodium bicarbonate) 5.64 and 5.95 (quartet: J = 16 Hz, -CH$_2$OCH(CH$_3$)$_2$); 6.31, 8.87τ )-CH$_2$-OCH (CH$_3$)$_2$ respectively). (Found: C, 51.6; H, 5.1; N, 6.7; S, 16.3. $C_{17}H_{20}N_2O_5S_2$ requires C, 51.5; H, 5.1; N, 6.1; S, 16.2%). $R_f$ 0.32 (system B), 0.65 (system C).

EXAMPLE 12

The reaction of 3-dichloroacetoxymethyl-7β-(2'-thienylacetamido)-ceph-3 -em-4-carboxylic acid with various alcohols Solutions of the acid (40 mg.) in each alcohol (0.5 ml.) were heated at 80° for half an hour. Samples (5 μl.) were spotted onto papers which were developed with solvent System C to about 30 cms. The papers were submitted for bioautograph against *Staph. aureus* C 864 and *E. cali* 573. The biological activities (the area of biologically active zone/the area of UV.-absorbent zone)

of the new spots (other than material remaining on the base line or travelling at the solvent front) are summarised in the table fofllowing Example 13.

EXAMPLE 13

The reaction between 3-dichloroacetoxymethyl-7β-(2'-thienylacetamido)-ceph-3-em-4carboxylic acid and phenol A mixture of the acid (0.5 g., 1.08 mmole.) and phenol (0.8 g., 5.3 mmole.) was heated at 80° for 8 minutes. The melt was cooled and dissolved in ethyl acetate (10 ml.). The insoluble material was filtered off and discarded, and the filtrate washed with water (2 × 10 ml.). Samples (5 μl.) were spotted onto papers which were developed with solvent System C to about 30 cms. The papers were submitted for bioautograph against *Staph. aureus* C 864 and *E. coli* 573. The results were estimated in the same manner as in Example 12 and are presented in the following table.

| Alcohol | $R_f$ | Staph.aureus | E.coli |
|---|---|---|---|
| a) Cyclohexanol | 0.57 | +++ | + |
| b) Bensylalcohol | 0.47 | +++ | + |
| c) Phenyl ethynyl alcohol | 0.56 | +++ | trace |
| d) Furfuryl alcohol, spot 1 | 0.25 | +++ | ++ |
| Furfuryl alcohol, spot 2 | 0.53 | +++ | trace |
| e) 2-Chloroethanol | 0.41 | +++ | trace |
| f) Phenol | 0.70 | +++ | + |

EXAMPLE 14

N-[7β-(2'-Thienylacetamido)ceph-3-em-3-ylmethyl]-thiazolium-4-carboxylate

3-Dichloroacetoxymethyl-7β-(2'-thienylacetamido)-ceph-3-em-4-carboxylic acid (3 g., 6.5 mmole.) was dissolved in 50%-aqueous acetone (50 ml.), and treated with thiazole (1.8 ml., 25.4 mmole.), and the solution heated at 50° for 30 minutes. The acetone was removed under vacuum and the aqueous layer extracted with ethyl acetate (2 × 10 ml.). The dissolved ethyl acetate was removed under reduced pressure and the aqueous residue passed down a column of Dowex 1 ($AcO^-$) (3 × 10 cms.) and eluted with water until the eluate did not show significant optical rotation. The eluates were freeze-dried. The freeze-dried solid was treated with methanol, when it crystallised without going into solution (800 mg., 29%), m.p. 169°–172° (decomp) $[\alpha]_D^{26} = 14.1°$ (c 1.03, acetone: water = 1.1), $\lambda_{max}$ (pH 6 phosphate buffer) 236–7 nm. ($\epsilon$ = 18,000), 264 nm. ($\epsilon$ = 10,000) (shoulder), $\nu_{max}$(Nujol) 1760 (β-lactam), 1692 (—CONH—), 1602 $cm^{-1}$ ($COO^-$). (Found: C, 45.6; H, 3.7; N, 9.4; S, 21.1 $C_{17}H_{15}N_3S_3O_4.1½H_2O$ requires C, 45.5; H, 4.0; N, 9.4; S, 21.4%). $R_f$ 0.14 (System B), 0.04 (System C).

EXAMPLE 15

3-(N-Pyrazolylmethyl)-7β-(2'-thienylacetamido)-ceph-3-em-4-carboxylic acid

3-Dichloroacetoxymethyl-7β-(2'-thienylacetamido)-ceph-3-em-4-carboxylic acid (3.2 g., 6.9 mmole.) was dissolved in 50%-aqueous acetone (60 ml.) and treated with pyrazole (1.6 g., 24 mmole.), and the solution heated at 50° for 35 minutes. The acetone was removed under reduced pressure, and the aqueous residue was extracted with ether (9 × 20 ml.). After drying, the ether was evaporated and the solid residue recrystallised from aqueous alcohol (1.3 g., 47%), mp. 180°–185° (decomp) $[\alpha]_D^{30} = 53.5°$ (c 1.01, ethanol), $\lambda_{max}$(ethanol) 236 nm. (β 14,000), 261 nm. ($\epsilon$ = 8,250) (shoulder), $\gamma_{max}$ (Nujol) 3272 (—NH), 1773 (β-lactam), 1712 (—COOH), 1660 and 1532 $cm^{-1}$ (—CONH—). (Found: C, 50.9; H, 4.2; N, 13.9; S, 15.7. $C_{17}H_{16}N_4S_2O_4$ requires C, 50.5; H, 4.0; N, 13.9; S, 15.9%). N.M.R. ($D_2O$, with $NaHCO_3$) 2.30, 3.62, 2.41τ (-N-C$\underline{H}$=C$\underline{H}$-C$\underline{H}$=N), $R_f$ 0.37 (Systems B), 0.12 (System C).

EXAMPLE 16

N-[7β-(2'-Thienylacetamido)ceph-3-em-3-ylmethyl]-5''-(β-hydroxyethyl)-4''-methylthiazolium-4-carboxylate 3-Dichloroacetoxymethyl-7β-(2'-thienylacetamido) ceph-3-em-4-carboxylic acid (1.0 g., 2.15 mmole) and 5-(β-hydroxyethyl)-4-methylthiazole (0.7 g., 4.9 mmole.) were dissolved in 50%-aqueous acetone (20 ml.) and the solution was heated at 50° for 30 minutes. The solution was cooled and the acetone removed under reduced pressure. The aqueous layer was extracted with ethyl acetate (2 × 10 mls.) and passed down a column of Dowex 1 ($AcO^-$) (2 × 8 cm.), and eluted with water until the eluate did not show any significant optical rotation. The eluate was freeze-dried to give a white solid (400 mg., 39%), m.p. 125–130°λ (decomp) $[\alpha]_D^{26} = 14.8°$ (c, 1.01, acetone-water = 1:1), $\lambda_{max}$ (pH6-phosphate buffer) 305 and 257 nm ($\epsilon$ 14,700 and 12,000 resp.), $\nu_{max}$ (Nujol) 1775 (β-lactam), 1670 and 1550 (—CONH—), 1615 ($—COO^-$) $cm^{-1}$. (Found: C, 47.7; H, 4.6; N, 8.1; S, 18.5. $C_{20}H_{21}N_3S_3O_5.1½ H_2O$ requires C, 47.7; H, 4.8; N, 8.3; S, 19.0%) $R_F$ 0.16 (System B), 0.04 (System C).

EXAMPLE 17

N-[4-Diphenylmethoxycarbonyl-7β-(2'-thienylacetamido) ceph-3-em-3ylmethylpyridinium chloride Diphenylmethyl 3-chloromethyl-7β-(2'-thienylacetamido) ceph-3-em-4-carboxylate (1 g.) was kept at 50° in dry pyridine (10 ml.) for 2 hours. The pyridine was removed at 30°/0.1 mm., and the residue partitioned between water and ethyl acetate. The aqueous layer was freed from organic solvents and freeze-dried to give a white solid, which was triturated with ether to give the title compound (760 mg., 65%), $[\alpha]_D^{23} = +280°$ (c 1.0, water), $\lambda\lambda_{max}$ (pH6-phosphate buffer)240nm ($\epsilon$ = 14,800), 249–250 nm ($\epsilon$ = 13,700) (both inflexions) $\nu_{max}$(Nujol) 1780 (β-lactam), 1742 (COOR), 1545 and 1680 $cm^{-1}$ (CONH). N.M.R. spectrum (Pyridine)3-1-C$\underline{H}_2$ at 5.75τ. (Found: C, 59.4; H, 4.7; N, 6.1; S, 9.9; Cl, 5.4 C $_{32}H_{28}N_3S_2O_4Cl.1½H_2O$ requires C, 59.5; H, 4.8; N, 6.5; S, 9.9; Cl 5.5%). The product carries a positive charge at pH 1.9 and at pH 7 (electrophoresis). It stains violet with the iodoplatinate spray reagent.

In a manner analogous to that described in Example 1(c) the diphenyl methyl esterifying group was removed by acid hydrolysis using trifluoroacetic acid in conjunction with anisole.

EXAMPLE 18

Diphenylmethyl 3-n-propoxymethyl-7β-2'-thienylacetamido-ceph-3-em-4-carboxylate A solution of diphenylmethyl 7β-(2'-thienylacetamido)-3-chloromethylceph-3-em-4-carboxylate (1.5 g., 2.8 mmole.) in acetone (80 ml.) was treated with a solution of sodium iodide (0.45 g., 3.0 mmole) in acetone (15 ml.). The solution was allowed to stand in the dark for 1 hour at room temperature. The solution was filtered and poured into water. The mixture was extracted with ether (3 × 15 ml.) and the ether extracts dried over magnesium sulphate and evaporated. The gum was dissolved in n-propanol (50 ml.) and treated with mercuric perchlorate hydrate (4 g., 9.6 mmole.). After 5 minutes the black precipitate was filtered on Kieselguhr. The filtrate was evaporated under reduced pressure and the residue was dissolved in ethyl acetate, filtered, washed with aqueous sodium bicarbonate and water, dried, and evaporated. The resulting gum was chromatographed on a silicic acid column (4.5 × 25 cms.) in benzene: ethyl acetate = 9:1. The fractions containing the n-propoxymethyl compond ($R_f$ ca. 0.7, ethyl acetate:benzene = 1:5, on silica gel G) were bulked and evaporated (0.6 g., Yield ca. 38%)

EXAMPLE 19

Preparation of 3-methoxymethyl-7β-(2'-thienylacetamido)ceph-3-em-4-carboxylic acid The title compound was prepared via the following reaction scheme (the steps are described in more detail below).

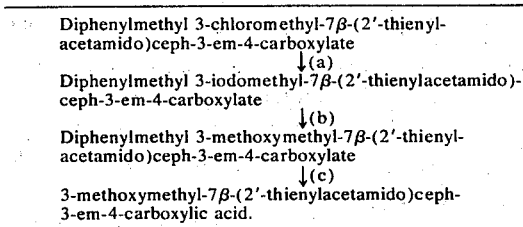

Diphenylmethyl 3-chloromethyl-7β-(2'-thienyl-acetamido)ceph-3-em-4-carboxylate
↓(a)
Diphenylmethyl 3-iodomethyl-7β-(2'-thienylacetamido)-ceph-3-em-4-carboxylate
↓(b)
Diphenylmethyl 3-methoxymethyl-7β-(2'-thienyl-acetamido)ceph-3-em-4-carboxylate
↓(c)
3-methoxymethyl-7β-(2'-thienylacetamido)ceph-3-em-4-carboxylic acid.

a. Diphenylmethyl 3-iodomethyl-7β-(2'-thienylacetamido)ceph-3-em-4-carboxylate Diphenylmethyl 3-chloromethyl-7β-(2'λ thienylacetamido)-ceph-3-em-4 -carboxylate (7.858 g., 14.5 mmole) was dissolved in acetone and reacted with sodium iodide (7.8 g., 50 mmole) in acetone (100 ml.) in the dark for 90 minutes. At the end of this time the solution was filtered and poured into water (750 ml.) containing sodium chloride and sodium thiosulphate. The oil was extracted with ether (4×), and the organic layer washed once with water and twice with brine, and dried and evaporated to a foam, which was crystallised from ethyl acetate (16 ml.) to give the title compound. The mother liquors were washed with sodium thiosulphate, water and brine, and were dried and evaporated to a foam (2.75 g., impure title compound, approx. 30% yield). Yield of crystalline material 60%, m.p. 155–161°C (decomp.), $[\alpha]_D^{28} = 86.3°$ (c 0.73; tetrahydrofuran), $\lambda_{max}$ (ethanol) 290 nm. (ε 8,400), $\nu_{max}$ (Nujol) 1773 (β-lactam), 1717 ($CO_2R$), and 1670 and 1520 cm.$^{-1}$ (-CONH-), N.M.R. (deuterochloroform) τ5.70 (2-proton broad singlet) ($CH_2I$) (Found: C, 51.6; H, 3.7; I, 19.7; N, 4.3; S, 10.2. $C_{27}H_{23}IN_2O_4S_2$ requires C, 51.3; H, 3.7; I, 20.1; N, 4.4; S, 10.2), $R_F$ 0.65 (Kieselgel G, benzene-ethylacetate=5:1) (T.L.C.).

b. Diphenylmethyl 3-methoxymethyl-7β-(2'-thienylacetamido)ceph-3-em-4-camboxylate A solution of diphenylmethyl 3-iodomethyl-7β-(2'-thienylacetamido)ceph-3-em-4-carboxylate (2.5 g., 3.96 mmole) in benzene (100 ml.) was treated with a solution of mercuric perchlorate (0.9 g.≈4 mmole) in methanol (25 ml.). After standing five minutes at room temperature, the solution was successively washed aqueous sodium hydrogen carbonate, aqueous sodium thiosulphate and water, and then evaporated under reduced pressure. The gum was dissolved in benzene/ethyl acetate (9:1) and the solution filtered under reduced pressure through a pad of silicic acid. The pad was then washed with the same solvent. The combined filtrates were evaporated and the gum dissolved in ethanol (15 ml). When the title compound separated as colourless prisms (0.61 g., 29%), m.p. 146°–147°, $[\alpha]_D^{25} + 15.6°$ (c 1, tetrahydrofuran), $\lambda_{max}$(ethanol) 235 (sh.), 260 (sh.)nm (ε 14,800, 9,100 respectively), $\nu_{max}$ (Nujol) 1786 β-lactam, 1725 (—COOR) 1668 and 1646 (—CONH) cm$^{-1}$., N.M.R. 5.76 (—C$\underline{H}_2$OCH$_3$), 6.80 τ (-CH$_2$OC$\underline{H}_3$), (Found: C, 63.1; H, 4.9; N, 5.1; S, 11.5. $C_{28}H_{26}N_2O_5S_2$ requires: C, 62.9; H, 4.9; N, 5.2; S, 12.0%).

c. 3-Methoxymethyl-7β-(2'-thienylacetamido)ceph-3-em-4-carboxylic acid

Diphenylmethyl 3-methoxymethyl-7β-(2'-thienylacetamido)-ceph-3-em-4-carboxylate (2 g.,) was dissolved in a mixture of trifluoroacetic acid (8 ml) and anisole (2 ml) and after 5 minutes the reagents removed under reduced pressure. The resulting gum was dissolved in ethyl acetate and poured into 60°–80° petroleum and the product recovered by filtration. This material crystallised from ethyl acetate as colourless prisms, m.p. 153°–157° (decomp.), $[\alpha]_D^{25} + 81.6°$(c 1, tetrahydrofuran), $\lambda_{max}$ (ethanol) 237, 260 (Sh.) nm (ε 13,700 and 7,700 respectively), $\nu_{max}$(Nujol) 1780 (β-latham), 1720 (-COOH), 1690 and 1524 cm$^{-1}$ (-CONH), N.M.R. 5,80 (-C$\underline{H}_2$OCH$_3$), 6.70τ (-CH$_2$OC$\underline{H}_3$), (Found: C, 49.2; H, 4.4; N, 7.5; S, 17.0. $C_{15}H_{16}N_2O_5S_2$ requires: C, 48.9; H, 4.4; N, 7.6; S, 17.4%).

EXAMPLE 20 a. Diphenylmethyl 3-(2'-oxocyclohexyl)methyl-7β-(2''-thienylacetamido)-ceph- 3-em-4-carboxylate A solution of diphenylmethyl 3-iodomethyl-7β-(2'-thienylacetamido)-ceph-3-em-4-carboxylate (8 g., 12.7 m.mole, in dry benzene was treated with N-(cyclohex-1-enyl)-pyrrolidine (4 g., 26.2 m.mole.) and refluxed for 5 minutes. The solution was then cooled and a mixture of 2N-hydrochloric acid (20 ml. and acetone (80 ml.) added. The suspension was well shaken until all the oil had dissolved and then ethyl acetate (300 ml.) and water (100 ml.) added. After shaking, the aqueous layer was separated and discarded and the organic layer washed with (a) aqueous sodium thiosulphate, (b) aqueous sodium bicarbonate, and (c) water, and then dried and evaporated. The foam was dissolved in ethyl acetate (25 ml.) and after 15 minutes the title compound filtered off, washed with ethanol and dried(4.5 g., 59%). This material crystallised from ethanol as colourless prisms, m.p. 167°–170°, $[\alpha]_D^{23} + 8.5°$ (c 1, tetrahydrofuran), $\lambda_{inf.}$ (ethanol) 260 nm ($\epsilon$ 7,500), $\nu_{max.}$(CHBr$_3$) 1780 ($\beta$-lactam), 1720 (COOR), 1702 (>=O), and 1682 and 1512 (—CONH—) cm.$^{-1}$, N.M.R. (CDCl$_3$) 7.3 – 9.0 $\tau$ (protons in cyclohexanone ring) (Found: C, 65.4; H, 5.4; N, 4.5; S, 10.7. C$_{33}$H$_{32}$N$_2$O$_5$S$_2$.¼H$_2$O requires C, 65.6; H, 5.4; N, 4.6; S, 10.6%).

b. Diphenylmethyl 7β-amino-3-(2′-oxocyclohexyl)methylceph-3-em-4-carboxylate; hydrogen p-toluenesulphonate A solution of diphenylmethyl 3-(2′-oxocyclohexyl)-methyl7β-(2′′-thienylacetamido)-ceph-3-em-4-carboxylate (2.25 g., 3.75 mmole) and pyridine (3.75 ml., 4.75 mmole.) in methylene chloride (30 ml.) was cooled to −10° and treated with a solution of phosphorus pentachloride (2.35 g., 11.3 m.mole.) in methylene dichloride (35 ml. over 5 minutes. The solution was stirred at −10° for 30 minutes. Methanol (37.5 ml.) was added at such a rate that the temperature did not rise above −10°, and when it had all been added, the temperature was allowed to rise to room temperature. After five hours standing the solution was cooled to −10° and treated with water (50 ml.), with vigorous stirring. Stirring was continued at room temperature for 30 minutes. The organic layer was separated and washed successively with dilute acetic acid, aqueous sodium bicarbonate and water, and then dried and evaporated. The gum was dissolved in ethyl acetate (20 ml.) and ether (50 ml.) and treated with p-toluenesulphonic acid (0.73 g., 7.7 m.mole.) in ethyl acetate (30 ml.). The title compound separated as colourless prisms (0.80 g., 33%). This material could be recrystallised from chloroform/ethyl acetate, m.p. 162°–166° (d), $[\alpha]_D$ - 0.9° (C 1, methylene chloride:methanol = 4:1 (v/v)), $\lambda_{max.}$ (EtOH) 259 nm ($\epsilon$ 6,900), $\nu_{max.}$ (Nujol) 1780 ($\beta$-lactam), 1718 (COOR), and 1700 (>=0) cm.$^{-1}$, N.M.R. (in (CD$_3$)$_2$SO), 7.30 (protons in cyclohexanone ring) 7.5 – 8.9$\tau$ (protons in cyclohexanone ring), (Found: C, 62.3; H, 5.7; N, 3.9; S, 9.4. C$_{34}$H$_{36}$N$_2$O$_7$S $_2$1/2H$_2$O requires C, 62.1; H, 5.7; N, 4.3; S, 9.7%).

c. 7β-(D-α-Amino-α-phenylacetamide)-3-(2′-oxocyclohexyl)methylceph-3-em-4-carboxylate A solution of N-(t-butoxycarbonyl)-D-phenylglycine (0.92 g., 3.35 m.mole.) in dry tetrahydrofuran (10 ml.) at −6° was treated with triethylamine (0.54 ml., 3.35 m.mole.) and then with a solution of isobutylchloroformate (0.53 g., 3.36 m.mole.) in dry tetrahydrofuran (4 ml.), at such a rate that the temperature did not rise above −6°. After 30 minutes stirring at room temperature the triethylammonium chloride was filtered off. The filtrate was added to a solution of diphenylmethyl 7β-amino-3-(2′-oxocyclohexyl)-methylceph-3-em-4-carboxylate, hydrogen-p-toluenesulphonate (1.5 g., 2.55 m.mole.) in acetonitrile (8 ml.) and N,N-dimethylacetamide)(4 ml.). After 60 minutes the solvents were removed under reduced pressure. A solution of the residue in ethyl acetate was washed with aqueous sodium bicarbonate and water and then dried and the solvent evaporated. The gum was treated with anisole (3 ml.) and trifluoroacetic acid (12 ml.), and after 5 minutes the reagents removed under vacuum. The oil was suspended in water (100 ml.) and treated with 10%-Amberlite LAl resin (OAc$^-$) in ether (50 ml.). After shaking, the aqueous layer was separated and washed with ethyl acetate (4 × 50 ml.) and then freeze-dried to give a white solid (700 mg., 68%), m.p. 150°–210°, $\lambda_{max.~(H2O)}$ 261 nm. ($\epsilon$ 6,600), $\nu_{max.}$ (H$_2$O) 261 nm. ($\epsilon$ 6,600), $\beta_{max.}$ (Nujol) 1766 ($\beta$-lactam), 1700 (>=0), 1680 and 1530 (—CONH—), and 1620 (—COO$^-$) cm.$^{-1}$, N.M.R. (in (CD$_3$)$_2$SO) 2.52 (phenyl) 7.0 – 0.0$\tau$(protons in cyclohexane ring) R$_f$ 0.17 (system B), 0.06 (system C). Electrophoresis at pH 1.9 gives 2 spots, both giving colours with ninhydrin. The faster, which does not absorb ultraviolet light corresponds in this behavior with α-phenylglycine. The major fraction absorbs U.V. light.

EXAMPLE 21

Sodium 3-(2′-oxocyclohexyl)methyl-7β-(2′′-thienylacetamido)-ceph-3-em-4-carboxylate Diphenylmethyl 3-(2′-oxocyclohexyl)methyl-7β-(2′′-thienylacetamido)-ceph-3-em-4-carboxylate (1.5 g., 2.5 m.mole, was dissolved in a mixture of anisole (3 ml.) and trifluoroacetic acid (10 ml.). After 5 minutes the reagents were removed under reduced pressure and the product precipitated by solution in ethyl acetate and pouring into petrol. The white solid so obtained was dissolved in acetone (80 ml.) and treated with 10%-sodium ethylhexanoate in acetone (12.5 ml., 7.5 m.mole.) when the title compound separated as colourless prisms (800 mg., 70%), $[\alpha]_D^{23} + 98.1°$ (c 1, H$_2$O), $\lambda_{max.}$ (H$_2$O) 236 nm ($\epsilon$ 13,100), $\lambda_{inf.}$ 260 nm ($\epsilon$ 5,900), $\beta_{max.}$ (Nujol) 1738 ($\beta$-lactam), 1690 ( >=0), 1645 and 1532 (-CONH-) and 1600 (COO$^-$) cm$^{-1}$, N.M.R. (D$_2$O) 7.0 - 9.0$\tau$ (protons in cyclohexanone ring) (Found: C, 51.4; H, 4.8; N, 5.6; S, 13.4. C$_{20}$H$_{21}$NaN$_2$O$_5$S$_2$.1/2H$_2$O requires: C, 51.6; H, 4.8; N,6.0; S, 13.8%). R$_f$ 0.48 (system B), 0.61 (system C).

EXAMPLE 22

Diphenylmethyl 3-bromoethyl-7β-2′-thienylacetamidoceph-3-em-4-carboxylate

Diphenylmethyl 3-hydroxymethyl-7β-2′-thienylacetamidoceph-3-em-4-carboxylate (520 mg. 1 m.mole.) in dry tetrahydrofuran (10 ml.) containing pyridine (79 mg., 1 m. mole.) was treated dropwise during 15 minutes with a solution of phosphorus tribromide (180 mg., 0.4 m.mole.) in dry tetrahydrofuran (3 ml.). After 1 hour at room temperature the mixture was evaporated, the residue shaken with benzene, and filtered. The filtrate was chromatographed on Kiesel 0.05 – 0.2 (E Merck A.G., Darmstadt, W. Germany), and the fractions eluted with benzene:ethyl acetate = 1:8, combined, and evaporated to give a gum which, on trituration with cold absolute ethanol, solidified. The solid (180 mg.) was washed with ether and dried in vacuo. $[\alpha]_D^{25}-33°$ (c, 1.0; tetrahydrofuran), $\lambda_{max}$ (tetrahydrofuran) 276 nm ($\epsilon$ 9,500), $\nu_{max.}$ (bromoform) 3390 (NH), 1780 ($\beta$-lactam), 1720 (CO$_2$CNPh$_2$), and 1500 and 1680 cm.$^{-1}$ (CONH), NMR (CDCl$_3$)6.2

(—CH₂-CONH), 4.20 and 5.07 (protons at the 6- and 7-positions), 5.72τ (—CH₂B), R_f 0.55 (Kieselgel GF 254, Ethyl acetate:benzene = 1;5) (Found: Br, 12.7; S, 11.2. C₂₇H₂₃BrN₂O₄S₂ requires C, 55.6; H, 4.0, Br, 13.7, N, 4.8; S, 11.0%).

EXAMPLE 23 a. Diphenylmethyl 7β-amino-3-isopropoxymethylceph-3-em-4-carboxylate, hydrogen p-toluenesulphonate.

3-Dichloroacetoxymethyl-7β-(2′-thienylacetamido)-ceph-3-em-4-carboxylic acid (14 g., 30.1 m.mole.) was refluxed in isopropanol (110 ml.) for 45 minutes. After filtration through a pad of Kieselguhr, the isopropanol solution was poured into water (1000 ml.) and the pH adjusted to 8.5. The solution was extracted with ethyl acetate (2 × 100 ml.) and the extract discarded. The solution was then acidified to pH 1.5 with 2N-hydrochloric acid and extracted with ethyl acetate (3 × 100 ml.). The ethyl acetate extracts were dried over magnesium sulfate, and evaporated. The gum was dissolved in ethyl acetate (40 ml.), and ether (60 ml.) added. The precipitate was filtered off and the filtrate evaporated to give an orange gum (5.9 g.).

A solution of the above orange gum (5.9 g.) in tetrahydrofuran (65 ml.) was treated with an excess of diphenyldiazomethane (prepared from 4.5 g. of benzophenone hydrazone) in ether (80 ml.). After one hour the solution was treated with glacial acetic acid (2 ml.), and evaporated. The resulting gum was chromatographed on a silicic acid column (4 × 15 cms.) with (a) benzene and (b) benzene:ethyl acetate = 9:1. Those fractions containing a substance R_f ca. 0.7 on thin-layer chromatography (silica gel GF 254, with benzene:ethyl acetate = 5:1) were combined and evaporated to give a pale yellow gum (1.73 g.), which was diphenylmethyl 3-isopropoxymethyl-7β-(2′-thienylacetamido)-ceph-3-em-4-carboxylate. The 7-sidechain was removed by the general method described in Example 3a, yielding the title compound (600 mg., 3.3% based on the dichloroacetoxymethyl compound) λ_max. (ethanol) 263 nm (ε 6,600), ν_max. 1792 (β-lactam), 1728 (COOR) and 1130 (SO₃⁻) cm.⁻¹ (Found: C, 61.1; H, 6.0; N, 4.3; S, 10.3. C₃₁H₃₄N₂O₇S₂ requires C, 61.0; H, 5.6; N, 4.6; S, 10.5%). N.M.R. (CDCl₃) 5.41 and 5.83 (quartet, J = 16 Hz, -C$\underline{H}$₂OCH(CH₃)₂), 6.62, 8.99 τ (-CH₂-C$\underline{H}$ (C$\underline{H}$₃)₂ respectively).

Another experiment afforded diphenylmethyl 3-isopropoxymethyl-7β-aminoceph-3-em-4-carboxylate in a crystalline condition, m.p. 157°–161° (d), [α]_D²⁸ -3° (C 1.0; ethanol), before the formation of the p-toluenesulphonic acid salt.

b. 7β-(d-α-Amino-α-phenylacetamide 3-isopropoxymethyl ceph-3-em-4-carboxylic acid Acylation of diphenylmethyl 7β-amino-3-isopropoxy-methylceph-3-em-4-carboxylate hydrogen-p-toluene sulphenate (0.94 g., 1.47 mmole.) with the mixed anhydride from N-(t-butoxycarbonyl)-D-phenylglycine (0.77 g., 3.06 m.mole.) and isobutylchloroformate, by the general method described in Example 3b, gave the title compound (0.46 g., 74%). [α]_D²⁸ + 45° (C 1, H₂O), ν_max (water) 260 nm (ε 6,900), ν_max. (Nujol) 1766 (β-lactam) and 1695 (COO⁻) cm.⁻¹., N.M.R. (D₂O) 5.26, 6.02, 8.67 τ (-C$\underline{H}$₂OC$\underline{H}$ (C$\underline{H}$₃)₂ respectively) R_f 0.76 (system A), 0.18 (system B). This material was contaminated by impurities not revealed on the chromatograms under ultra-violet light; the main impurity is probably α-phenylglycine (ca. 30%) (Found: S:N = 1:4.1. Calc. for C₁₉H₂₃N₃O ₅S: S:N = 1:3).

Biological results of compounds prepared in Examples are given in the following table.

| Compound of Ex. No. | Tube Dilution Assay(g/ml.) | | | | | | | | | | Mouse Protection (1050/mg./kg./dose) | | |
|---|---|---|---|---|---|---|---|---|---|---|---|---|---|
| | Gram Positive | | | | | | Gram Negative | | | | | | |
| | Staph. aureus 604 | Staph. aureus 663 | Staph. aureus 3452 | Staph. aureus 11092 | Staph. aureus 11127 | Strep. faecalis 850 | E.coli 573 | S.typhi-murium 804 | Pr.mir-abilis 431 | Ps.pyo-cyanea 150 | S.aureus 663(S.C.)* | S.aureus 11127(S.C.)* | HOUR** |
| 6 | 0.62 | 0.31 | 2 | | 3.1 | | 125 | 125 | 125 | >250 | 3 | | <1.0 |
| 8a+ | 4 | 1 | 2 | | | 62 | | | | | | >50 | 2.5 |
| 14 | 1.25 | 0.02 | <0.5 | | | | 16 | 16 | 31 | >250 | <6 | | <1.0 |
| 15 | 0.6 | 0.03 | 8.0 | | | | 62 | 62 | 62 | 62 | | | 1.0 |
| 16 | 0.16 | 0.02 | <0.5 | | | | 8 | 16 | 62 | >250 | <6 | | < 1.0 |
| 19a+ | 16 | 1 | 8 | | 8 | 125 | | | | | | >50 | 2.8 |
| 20a | 0.6 | 0.6 | 2 | | 2 | 62 | 125 | 62 | 62 | >250 | | | |
| 21 | 0.3 | 0.02 | <0.5 | | <0.5 | 125 | 250 | 250 | 62 | >250 | | | |

\* = subcutaneous
HOUR** = % recovery of the antibiotic from the urine of female rats following oral administration of the antibiotic.
+ = denotes tests carried out on the free acid

We claim:
1. A compound of the formula

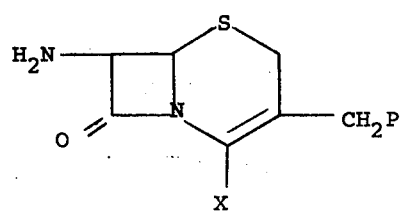

where P is chloro, bromo, iodo, formyloxy, isothiocyanato or haloacetoxy and X is carboxy, protected carboxy or a group COOM wherein M is an alkali metal.

* * * * *